US006177391B1

(12) United States Patent
Zafar

(10) Patent No.: US 6,177,391 B1
(45) Date of Patent: Jan. 23, 2001

(54) ONE TIME USE DISPOSABLE SOAP AND METHOD OF MAKING

(76) Inventor: Alam Zafar, 8100 Shore Front Pkwy. #12K, Rockaway Beach, NY (US) 11692

( * ) Notice: Under 35 U.S.C. 154(b), the term of this patent shall be extended for 0 days.

(21) Appl. No.: 09/321,042

(22) Filed: May 27, 2999

(51) Int. Cl.[7] ..... A61K 7/40; A61K 7/50; A24F 7/00

(52) U.S. Cl. ..... 510/131; 510/129; 510/130; 510/137; 206/85; 206/86; 206/104; 206/233

(58) Field of Search ..... 510/129, 130, 510/131, 137; 206/85, 86, 104, 233

(56) References Cited

U.S. PATENT DOCUMENTS 4,998,984 * 3/1991 McClendon ..... 206/205
5,213,884 * 5/1993 Fellows ..... 428/240
5,320,772 * 6/1994 Tricca ..... 252/160
5,409,747 * 4/1995 Pearlstein et al. ..... 428/34.2
5,415,276 * 5/1995 Welton ..... 206/63.5
5,971,142 * 10/1999 Jones ..... 206/233

* cited by examiner

*Primary Examiner*—Necholus Ogden

(57) ABSTRACT

A one time use disposable soap. The soap includes a substrate, a cleansing composition, and a holder. The substrate is dissolvable in water. The cleansing composition is impregnated in the substrate so as to form a dry and cleanser impregnated substrate. The dry and cleanser impregnated substrate is not laid hold on to prevent exposure and evaporation of the cleansing composition, since the dry and cleanser impregnated substrate is dry. The holder removably holds at least one stacked dry and cleanser impregnated substrate. When the dry and cleanser impregnated substrate is removed from the holder and subjected to water, the substrate dissolves leaving the cleansing composition dissolved in the water for cleansing.

5 Claims, 5 Drawing Sheets

ONE TIME USE DISPOSABLE SOAP AND METHOD OF MAKING

BACKGROUND OF THE INVENTION

1. Field of the Invention

The present invention relates to a soap. More particularly, the present invention relates to a one time use disposable soap and method of making.

2. Description of the Prior Art

Nowadays public places are equipped with regular soap bars of liquid soap jars. Both of these situations are unhygienic.

Everyday a large number of people use the same bar or the same jar to wash their hands. Some are healthy, and some are not. Some of them might carry germs which are contagious. In some cases these germs may stay and transmit to other people later on. In some instances, people even spread the mess all over the places, especially when a number of children use the same bathroom.

Women with long nails might experience difficulty when using soap bars or jars. In addition, germs may go under their nails and stay there. Later on, these germs may be transmitted to themselves while eating or transmitted to their children while hugging and kissing.

Furthermore, in most of the cases, children do not take the preventive measures which are needed while using public bathrooms.

In a famous TV program named 20/20 that aired on Jul. 12, 1999 on ABC channel 7, it was claimed that the inadequacies and unhygienic conditions in public bathrooms spread 58% of the germs in the community.

Numerous innovations for cleansing substrates have been provided in the prior art that will be described. Even though these innovations may be suitable for the specific individual purposes to which they address, however, they differ from the present invention.

FOR EXAMPLE, U.S. Pat. No. RE. 29,052 to Bucalo teaches a roll of toilet paper which has web portions where the web is folded upon itself and provided with an inner film of cleansing composition and an outer barrier layer so that the film of cleansing composition cannot spread through the convolutions of the roll while at the same time the folded web portions will become unfolded during unwinding of the roll to expose the cleansing composition. After the film of cleansing composition and barrier layer are respectively deposited at opposite faces of the web at preselected areas therealong the web is folded upon itself at the areas where the film of cleansing composition is located and then the film of cleansing composition at each folded web portion is frozen to retain each web portion in its folded condition during winding of the web into a roll.

ANOTHER EXAMPLE, U.S. Pat. No. 4,045,364 to Richter teaches a disposable paper with a slightly abrasive surface impregnated with an iodophor and detergent that is an excellent germicidal pre-wash in the surgical scrub routine or in any situation where it is important to impede the growth of microorganisms. By using substantially dry impregnated papers the product may be packaged and stored for at least 18 months without undue deterioration. In the presence of undue moisture, the paper degrades too fast for adequate storage.

STILL ANOTHER EXAMPLE, U.S. Pat. No. 4,998,984 to McClendon teaches a prepackaged single use disposable wiper pad or towelette that is saturated with a disinfecting liquid is prepared. The wiper pad is effective to disinfect inanimate surfaces such as telephone mouthpiece or toilet seat against a broad spectrum of infectious microorganisms including the HIV-1 or AIDS virus. The wiper pad is of a size which fits in a pocket or purse and makes it convenient to be carried safely by a person and poses no problem in disposing such as by flushing in a toilet.

YET ANOTHER EXAMPLE, U.S. Pat. No. 5,213,884 to Fellows teaches a tissue suitable for use in the disinfection of hard surfaces, instruments, and human or animal skin or as a sheet inclusion in a washing process for the purpose of disinfection or bleaching. The tissue comprises first and second substrate layers which are bonded together with an adhesive polymer. This polymer also retains solid particles between the layers, which particles, when dampened with a suitable liquid become active and release chlorine. Preferably, the adhesive polymer comprises either a copolyester, copolyamide or polyethylene hot melt adhesive powder or an ethylene vinyl acetate (EVA) or modified EVA hot melt adhesive powder with a particle size between 0 and 750 microns inclusive. Preferably also, the chlorine release agent comprises sodium dichloroisocyanurate dihydrate which is mixed with the adhesive polymer and applied between the substrate layers in coating weights between 2 and 35 grams per square meter inclusive to yield active solutions of between 10 and 10,000 parts per million available chlorine when the tissue is dampened with water.

It is apparent that numerous innovations for cleansing substrates have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a one time use disposable soap and method of making that avoids the disadvantages of the prior art.

ANOTHER OBJECT of the present invention is to provide a one time use disposable soap and method of making that is simple and inexpensive to manufacture.

STILL ANOTHER OBJECT of the present invention is to provide a one time use disposable soap and method of making that is simple to use.

BRIEFLY STATED, YET ANOTHER OBJECT of the present invention is to provide a one time use disposable soap. The soap includes a substrate, a cleansing composition, and a holder. The substrate is dissolvable in water. The cleansing composition is impregnated in the substrate so as to form a dry and cleanser impregnated substrate. The dry and cleanser impregnated substrate is not laid hold on to prevent exposure and evaporation of the cleansing composition, since the dry and cleanser impregnated substrate is dry. The holder removably holds at least one stacked dry and cleanser impregnated substrate. When the dry and cleanser impregnated substrate is removed from the holder and subjected to water, the substrate dissolves leaving the cleansing composition dissolved in the water for cleansing.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figure 1:
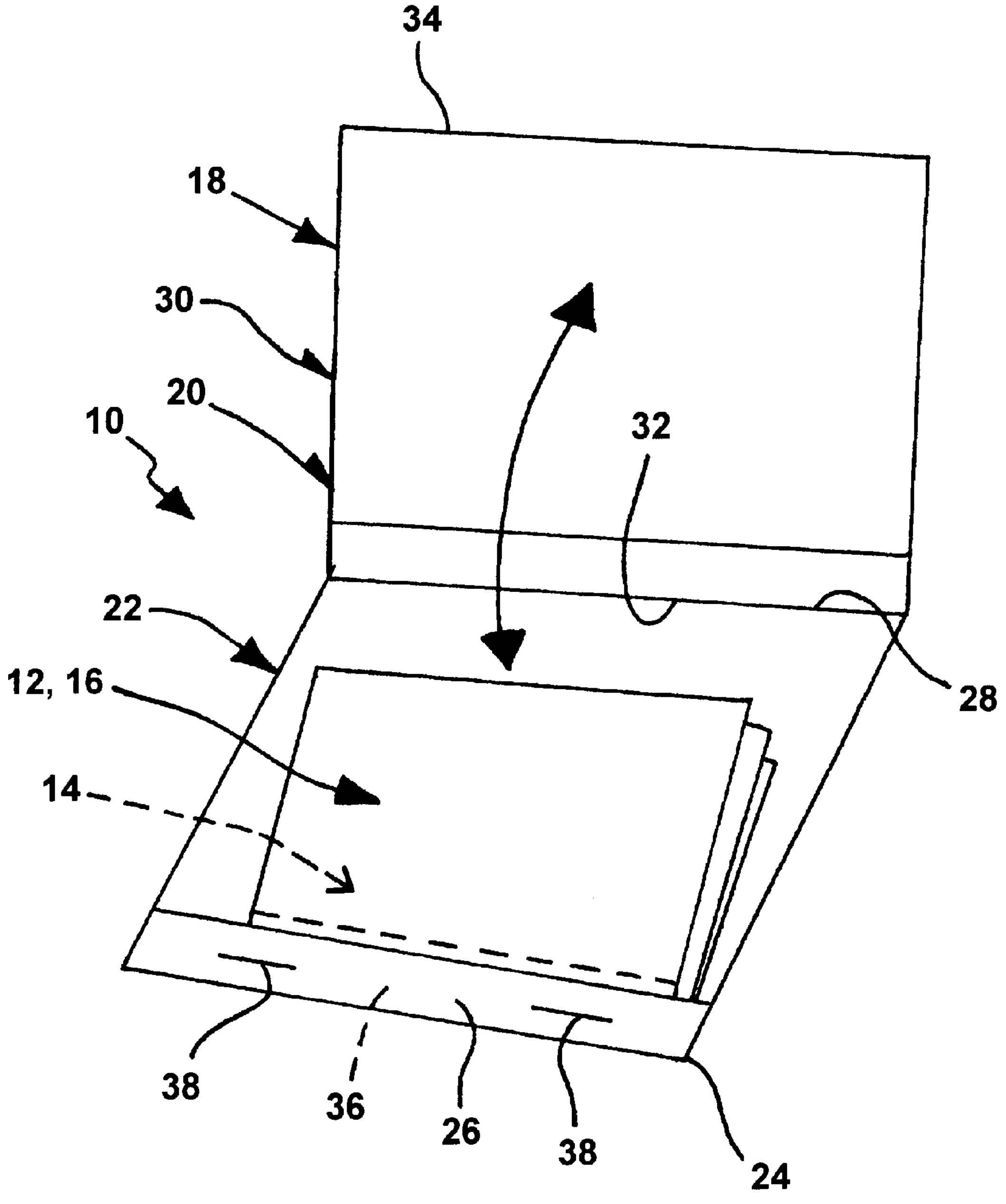
FIG. 1 is a diagrammatic perspective view of the present invention.
Figure 2A:
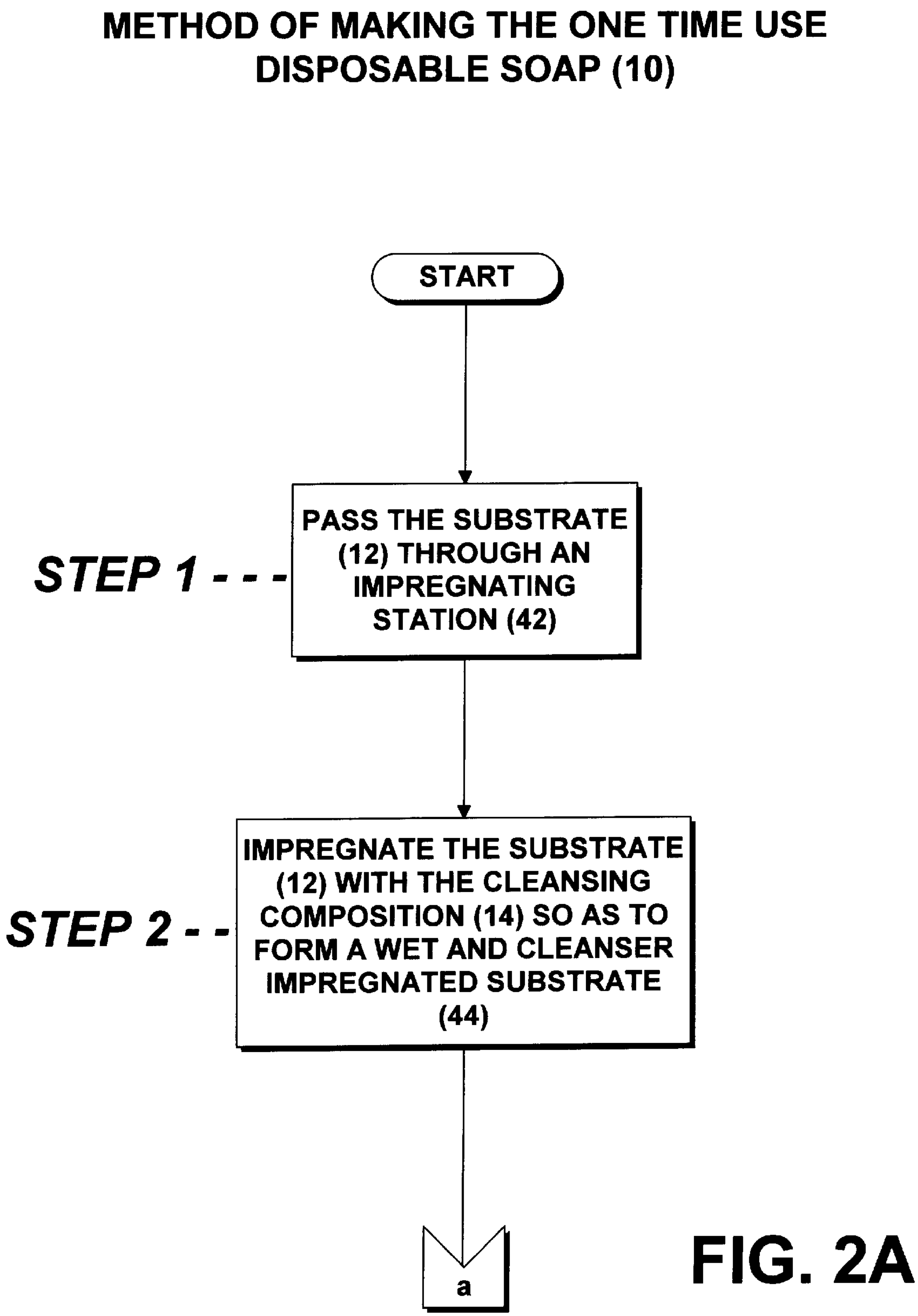
FIGS. 2A–2D are a process flow for making the present invention.
Figure 2B:
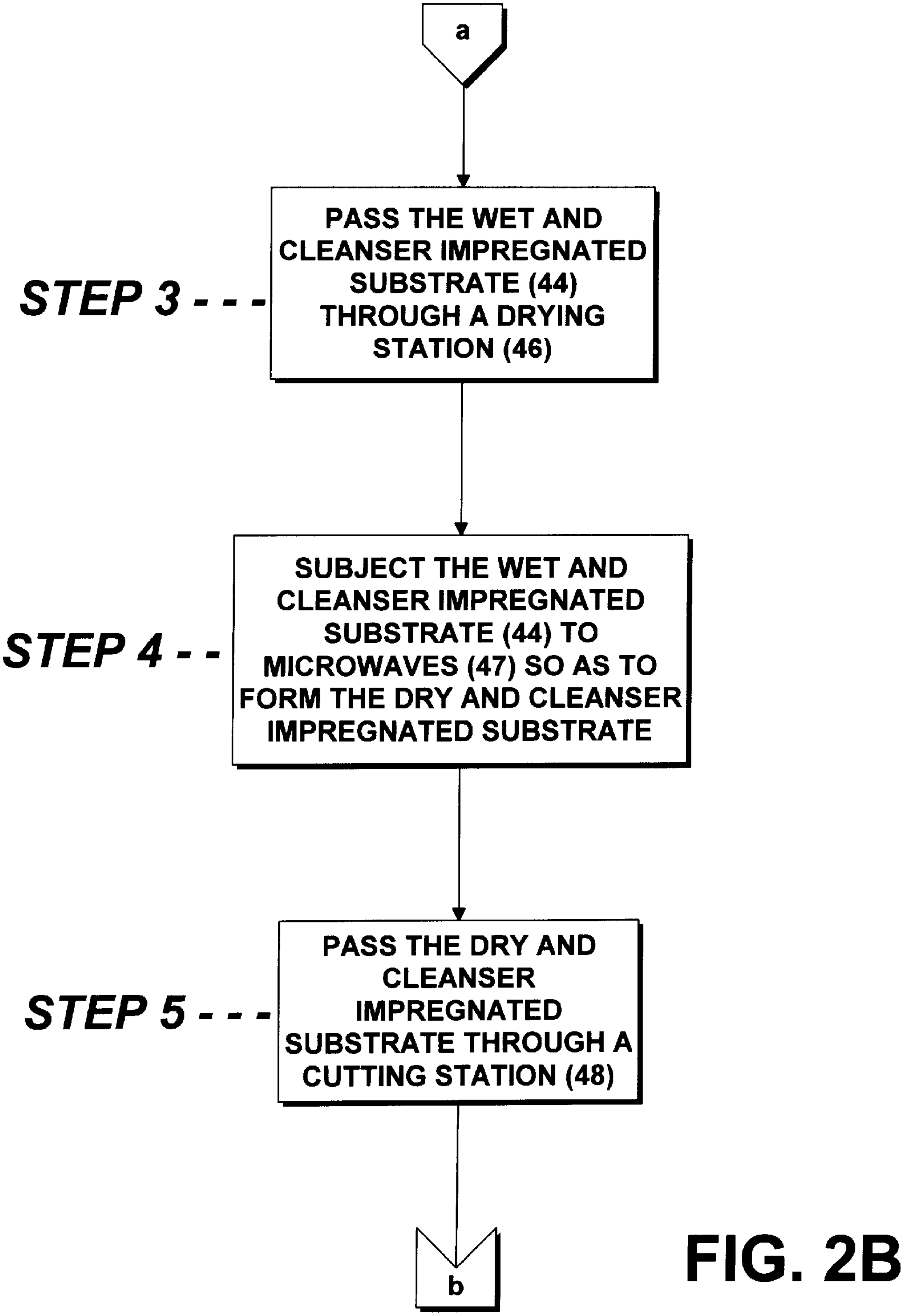
Figure 2C:
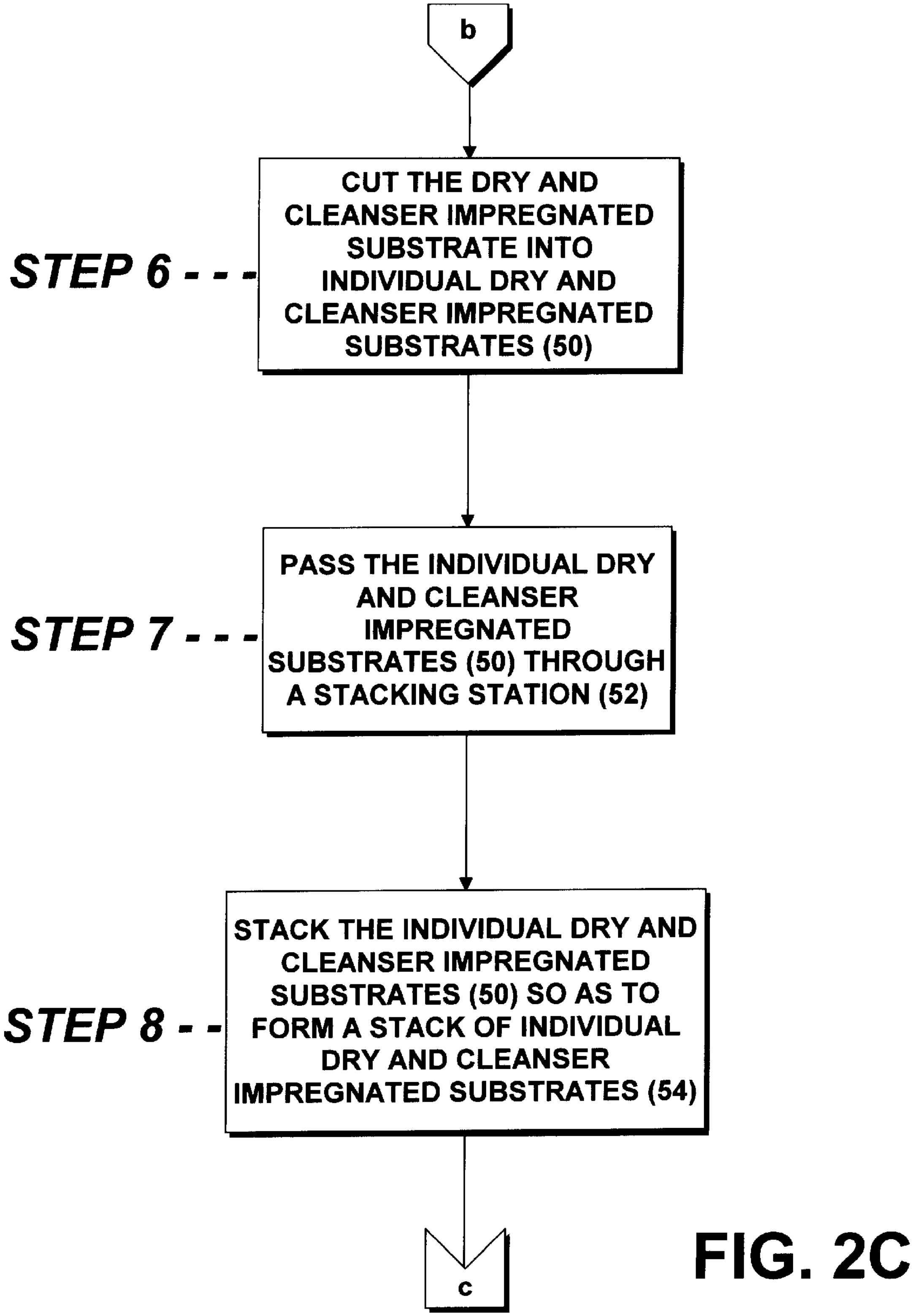
Figure 2D:
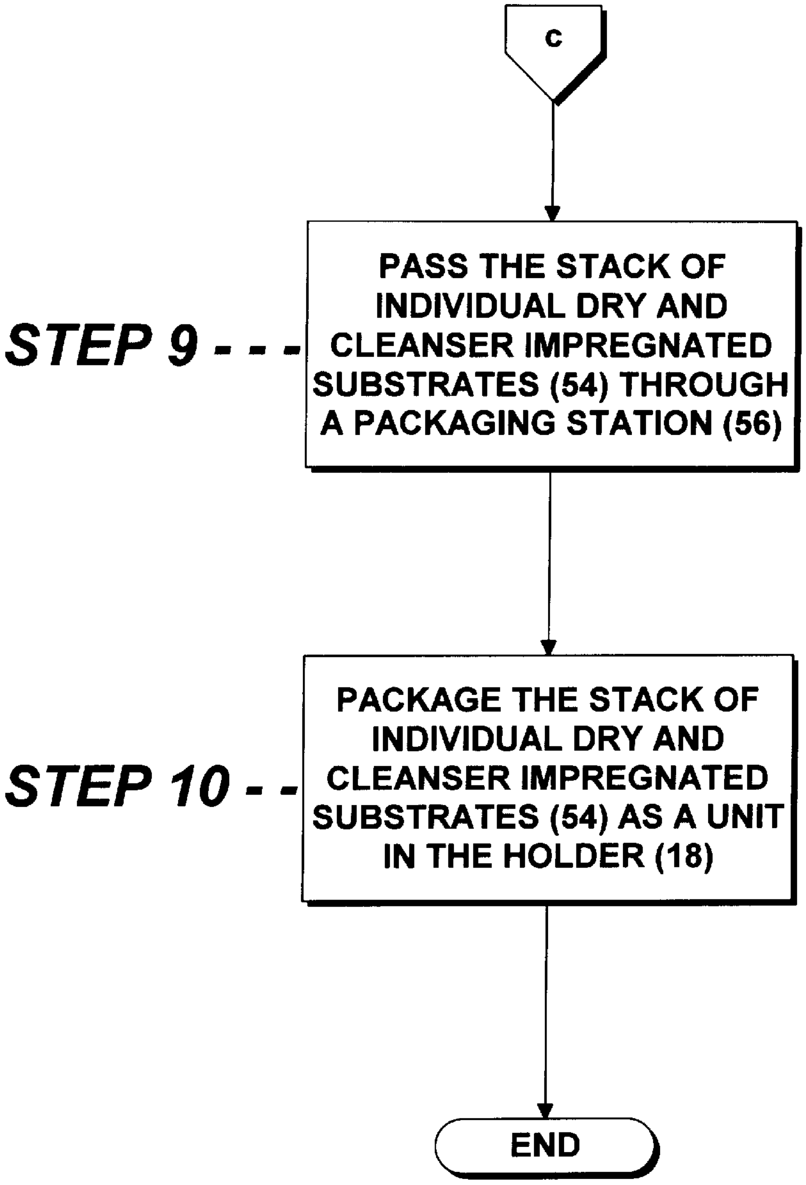

| LIST OF REFERENCE NUMERALS UTILIZED IN THE DRAWING | |
|---|---|
| 10 | one time use disposable soap of the present invention |
| 12 | substrate |
| 14 | cleansing composition |
| 16 | dry and cleanser impregnated substrate |
| 18 | holder |
| 20 | cover of holder 18 |
| 22 | back portion of cover 20 of holder 18 |
| 24 | lowermost edge of back portion 22 of cover 20 of holder 18 |
| 26 | upturned lip formed by lowermost edge 24 of back portion 22 of cover 20 of holder 18 |
| 28 | uppermost edge of back portion 22 of cover 20 of holder 18 |
| 30 | front flap of cover 20 of holder 18 |
| 32 | uppermost edge of front flap 30 of cover 20 of holder 18 |
| 34 | lowermost edge of front flap 30 of cover 20 of holder 18 |
| 36 | common edge of at least one stacked dry and cleanser impregnated substrate 16 |
| 38 | at least one staple |
| 40 | perforations extending across at least one stacked dry and cleanser impregnated substrate 16 |
| 42 | impregnating station |
| 44 | wet and cleanser impregnated substrate |
| 46 | drying station |
| 47 | microwaves |
| 48 | cutting station |
| 50 | individual dry and cleanser impregnated substrates |
| 52 | stacking station |
| 54 | stack of individual dry and cleanser impregnated substrates |
| 56 | packaging station |

DETAILED DESCRIPTION OF THE PREFERRED EMBODIMENT

Referring now to the figures, in which like numerals indicate like parts, and particularly to FIG. 1, which is a diagrammatic perspective view of the present invention, the one time use disposable soap of the present invention is shown generally at 10.

The one time use disposable soap 10 comprises a substrate 12 being dissolvable in water and being a tissue.

The one time use disposable soap 10 further comprises a cleansing composition 14 impregnated in the substrate 12 so as to form a dry and cleanser impregnated substrate 16.

The cleansing composition 14 is at least one of chlorine and iodophor and detergent.

The dry and cleanser impregnated substrate 16 is not laid hold on to prevent exposure and evaporation of the cleansing composition 14, since the dry and cleanser impregnated substrate 16 is dry.

The one time use disposable soap 10 further comprises a holder 18 removably holding at least one stacked dry and cleanser impregnated substrate 16.

When the dry and cleanser impregnated substrate 16 is removed from the holder 18 and subjected to water, the substrate 12 dissolves leaving the cleansing composition 14 dissolved in the water for cleansing.

The holder 18 comprises a cover 20 that is cardboard and has a back portion 22 with a lowermost edge 24 formed into an upturned lip 26 and an uppermost edge 28.

The cover 20 of the holder 18 further has a front flap 30 with an uppermost edge 32 that is foldingly attached to the uppermost edge 28 of the back portion 22 of the cover 20 of the holder 18 and a lowermost edge 34 that replaceably and selectively engages in the upturned lip 26 formed on the lowermost edge 24 of the back portion 22 of the cover 20 of the holder 18.

The at least one stacked dry and cleanser impregnated substrate 16 has a common edge 36 that is captured in the upturned lip 26 formed on the lowermost edge 24 of the back portion 22 of the cover 20 of the holder 18, with the at least one stacked dry and cleanser impregnated substrate 16 extending along the back portion 22 of the cover 20 of the holder 18.

The common edge 36 of the at least one stacked dry and cleanser impregnated substrate 16 is retained in the upturned lip 26 formed on the lowermost edge 24 of the back portion 22 of the cover 20 of the holder 18, by at least one staple 38 that passes through the upturned lip 26 formed on the lowermost edge 24 of the back portion 22 of the cover 20 of the holder 18 and the common edge 36 of the at least one stacked dry and cleanser impregnated substrate 16.

The at least one stacked dry and cleanser impregnated substrate 16 is removed from the cover 20 of the holder 18, by perforations 40 that extend across the at least one stacked dry and cleanser impregnated substrate 16, just above the upturned lip 26 formed on the lowermost edge 24 of the back portion 22 of the cover 20 of the holder 18.

When the at least one stacked dry and cleanser impregnated substrate 16 is to be removed from the cover 20 of the holder 18, one merely removes the lowermost edge 34 of the front flap 30 of the cover 20 of the holder 18 from the upturned lip 26 formed on the lowermost edge 24 of the back portion 22 of the cover 20 of the holder 18, opens the front flap 30 of the cover 20 of the holder 18 to expose the at least one stacked dry and cleanser impregnated substrate 16 that was protected by the front flap 30 of the cover 20 of the holder 18, grabs the at least one stacked dry and cleanser impregnated substrate 16, and tears the at least one stacked dry and cleanser impregnated substrate 16 off at the perforations 40 thereacross.

The method of making the one time use disposable soap 10 can best be seen in FIGS. 2A–2D, which are a process flow for making the present invention, and as such, will be discussed with reference thereto.

STEP 1: Pass the substrate 12 through an impregnating station 42.

STEP 2: Impregnate the substrate 12 with the cleansing composition 14 so as to form a wet and cleanser impregnated substrate 44.

STEP 3: Pass the wet and cleanser impregnated substrate 44 through a drying station 46.

STEP 4: Subject the wet and cleanser impregnated substrate 44 to microwaves 47 so as to form the dry and cleanser impregnated substrate 16.

STEP 5: Pass the dry and cleanser impregnated substrate 16 through a cutting station 48.

STEP 6: Cut the dry and cleanser impregnated substrate 16 into individual dry and cleanser impregnated substrates 50.

STEP 7: Pass the individual dry and cleanser impregnated substrates 50 through a stacking station 52.

STEP 8: Stack the individual dry and cleanser impregnated substrates 50 so as to form a stack of individual dry and cleanser impregnated substrates 54.

STEP 9: Pass the stack of individual dry and cleanser impregnated substrates 54 through a packaging station 56.

STEP 10: Package the stack of individual dry and cleanser impregnated substrates 54 as a unit in the holder 18.

It will be understood that each of the elements described above, or two or more together, may also find a useful application in other types of constructions differing from the types described above.

While the invention has been illustrated and described as embodied in a one time use disposable soap and method of making, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An article of manufacture for use as a disposable soap comprising:

a) a tissue being dissolvable in water;

b) a cleansing composition consisting of chlorine, iodophor and a detergent which is impregnated in said tissue so as to form a dry and cleanser impregnated tissue; said tissue being not laid hold on to prevent exposure and evaporation of said cleansing composition, since said tissue is dry; and c) a holder holding at least one stacked, dry and cleanser impregnated tissue, and when said tissue is removed from said holder and subjected to water, said tissue dissolves leaving said cleansing composition dissolved in the water for cleansing; said holder comprising a cover that has:

a) a back portion with:
   i) a lowermost edge formed into an upturned lip; and
   ii) an uppermost edge; and b) a front flap with:
   i) an uppermost edge that is folded and attached to said uppermost edge of said back portion of said cover of said holder; and
   ii) a lowermost edge that engages in said upturned lip formed on said lowermost edge of said back portion of said cover of said holder.

2. The article of manufacture according to claim 1, wherein said cover of said holder is cardboard.

3. The article of manufacture according to claim 1, wherein said at least one stacked, dry and cleanser impregnated tissue has a common edge that is captured in said upturned lip formed on said lowermost edge of said back portion of said cover of said holder, with at least one stacked, dry and cleanser impregnated tissue extending along said back portion of said cover of said holder.

4. The article of manufacture according to claim 3, wherein said common edge of said at least one stacked, dry and cleanser impregnated tissue is retained in said upturned lip formed on said lowermost edge of said back portion of said cover of said holder, by at least one staple passing through said upturned lip formed on said lower most edge of said back portion of said cover of said holder and said common edge of at least one stacked dry, and cleanser impregnated tissue.

5. The article of manufacture according to claim 1, wherein said at least one stacked, dry and cleanser impregnated tissue is removed from said cover of said holder, by perforations that extend across said at least one stacked, dry and cleanser impregnated tissue, just above said upturned lip formed on said lowermost edge of said back portion of said cover of said holder, and when said at least one stacked, dry and cleanser impregnated tissue is to be removed from said cover of said holder, one removes said lowermost edge of said from flap of said cover of said holder from said upturned lip formed on said lowermost edge of said back portion of said cover of said holder, to expose said at least one stacked, dry and cleanser impregnated tissue that was protected by said front flap of said cover of said cover of said holder, grabs at least one stacked dry and cleanser impregnated tissue, and tears said stacked, dry and cleanser impregnated substrate off at said perforations.

* * * * *

UNITED STATES PATENT AND TRADEMARK OFFICE

CERTIFICATE OF CORRECTION

PATENT NO. : 6,177,391

DATED : January 23, 2001

INVENTOR(S) : Zafar, Alam

It is certified that error appears in the above-identified patent and that said Letters Patent is hereby corrected as shown below:

One the title page, item [54] after "Disposable" insert therefore -- Tissue Paper --

Signed and Sealed this

Twenty-second Day of May, 2001

*Attest:*

NICHOLAS P. GODICI

*Attesting Officer* *Acting Director of the United States Patent and Trademark Office*